United States Patent [19]

Katsuragi et al.

[11] Patent Number: 5,756,543
[45] Date of Patent: May 26, 1998

[54] BITTERNESS-RELIEVING AGENT

[75] Inventors: Yoshihisa Katsuragi; Yoko Sugiura; Shigeyuki Ono; Kazuya Otsuji, all of Ibaragi, Japan

[73] Assignee: Kao Corporation, Tokyo, Japan

[21] Appl. No.: 616,192

[22] Filed: Mar. 15, 1996

[30] Foreign Application Priority Data

Mar. 15, 1995 [JP] Japan ................... 7-055357
Jun. 6, 1995 [JP] Japan ................... 7-139259

[51] Int. Cl.$^6$ .................. A61K 31/229; A61K 31/22; A61K 31/23
[52] U.S. Cl. .................. 514/547; 514/549; 514/552
[58] Field of Search ................ 514/549, 552, 514/547

[56] References Cited

U.S. PATENT DOCUMENTS 4,025,540  5/1977  Kleemann et al. ................ 260/410.7
5,434,182  7/1995  Isaacs et al. ................ 514/546
5,456,926  10/1995  Hill et al. ................ 426/73
5,505,982  4/1996  Krawczyk et al. ................ 426/660

FOREIGN PATENT DOCUMENTS 0014362  8/1980  European Pat. Off.
6245728  9/1994  Japan.

*Primary Examiner*—Raymond Henley, III
*Attorney, Agent, or Firm*—Birch, Stewart, Kolasch & Birch, LLP

[57] ABSTRACT

A bitterness-relieving agent which comprises an ester of a mono- or diglyceride with a polycarboxylic acid or a salt of the same, and a medicinal composition for oral use, a food, a cosmetic and a feed containing this bitterness-relieving agent. Because of being excellent in the effect of relieving bitterness, the bitterness-relieving agent of the present invention can be used in medicinal compositions for oral use, foods and cosmetics having bitter taste.

38 Claims, No Drawings

1

BITTERNESS-RELIEVING AGENT

FIELD OF THE INVENTION

This invention relates to a bitterness-relieving agent. More particularly, it relates to a bitterness-relieving agent which is capable of effectively relieving the bitterness when added to a medicinal composition for oral use, a food or a cosmetic tasting bitter.

BACKGROUND OF THE INVENTION

Tastes can be roughly classified into five fundamental ones (i.e., sweetness, saltiness, sourness, body and bitterness). Among these tastes, bitterness frequently causes unpleasantness. In the field of pharmacy, in particular, most of drugs have bitter taste, as the proverb says "Good medicine tastes bitter". Accordingly, it is an important problem in the drug manufacturing processes to mask the bitterness.

In the drug industry, it has been the main practice to mask bitterness by sugar-coating (in the case of tablets), or film-coating with the use of polymers (in the case of sugar-coating tablets, granules and grains). In the case of solid preparations in general, attempts have been also made to mask bitterness by microencapsulation, with the use of inclusion compounds (JP-A-3-236316; the term "JP-A" as used herein means an "unexamined published Japanese patent application"), or insolubilization of drugs via chemical modification. However, each of these methods suffers from some problems, for example, the bitterness cannot be completely masked thereby, a complicated procedure is required, or the application range thereof is restricted to particular drugs. The problem of relieving bitterness is further serious in the case of liquid drugs. Since no coating is applicable to liquid preparations, attempts have been made to mask bitterness by blending sugars or organic acids at high concentration or adding flavors. However, each of these methods fails to give any complete masking effect. Liquid drugs and dry syrups to be dissolved before using are frequently administered in particular, to infants and children who cannot well take solid drugs such as tablets and granules. Thus it is a serious problem in liquid drugs to mask bitterness.

Regarding foods, there arises the problem of bitterness in various foods, for example, the offensive tastes caused mainly by peptides and amino acids obtained from protein hydrolyzates and the bitterness of fruit juices. With the recent tendency toward healthful diets, there have been marketed a number of health foods of various types. Among these products, extracts originating in plants (for example, gymnemic acid, aloe) show intense bitterness. It is essentially required in many cases to eliminate offensive tastes from foods, since the qualities of the foods per se are deteriorated thereby. Examples of the existing methods for eliminating offensive taste components comprising mainly bitter components from foods include a method with the use of an adsorbent (U.S. Pat. No 4,282,264 corresponding to EP14362 and JP-A-55-108254, JP-A-60-91969), one with the use of an inclusion compound (JP-A-61-40260, JP-A-2-283246), one wherein a sweetener is added (JP-A-60-9774) and one wherein bitter components such as peptides are decomposed with enzymes and eliminated (JP-A-2-207768). Further, it has been a practice to modify food materials by preliminarily removing tissues containing offensive taste components such as bitter components therefrom. However, these methods each suffers from some problems, for example, the bitterness cannot be completely suppressed thereby or the taste of a food is changed thereby.

In some foods, it is necessary to not completely eliminate the offensive taste components mainly comprising bitter components. That is to say, the bitterness should be controlled, for example, eliminating the discomfort bitterness only, in these cases. Examples of such foods include luxury drinks (for example, coffee, black tea, green tea) alcoholic drinks (for example, beer, whisky) some soft drinks (for example, vegetable juice) and spicy vegetables (for example, edible wild plants). In these foods, namely, it is required not to completely eliminate the bitterness but control the same.

Regarding cosmetics, it is preferable that no component shows any bitterness particularly in lotions, mouse wash agents, tooth pastes, etc. to be applied to the face or the oral cavity. However, some surfactants and flavors employed in these products show bitterness, which restricts the type and content of such a component at using. The conventional method for relieving bitterness comprises adding sweeteners or specific flavors. However, there is a problem that this method exerts only an unsatisfactory effect on a component with an intense bitterness.

Accordingly, an object of the present invention is to provide a bitterness-relieving agent, which exerts an excellent effect of relieving bitterness on drugs, foods or cosmetics containing offensive taste components such as bitter components while causing neither any harm nor any change in the taste in the case of a food. Also, the present invention provides medicinal compositions for oral use, foods or cosmetics containing the above-mentioned bitterness-relieving agent.

Under these circumstances, the present inventors have conducted extensive studies. As a result, they have successfully found out that an ester of a mono- or diglyceride with a polycarboxylic acid or a salt of the same largely contributes to the relief of bitterness, thus completing the present invention.

SUMMARY OF THE INVENTION

Accordingly, the present invention provides a bitterness-relieving agent which comprises an ester of a mono- or diglyceride with a polycarboxylic acid or a salt of the same. The present invention also provides medicinal compositions for oral use, foods and cosmetics containing the above-mentioned bitterness-relieving agent.

DETAILED DESCRIPTION OF THE INVENTION

The ester of a mono- or diglyceride with a polycarboxylic acid to be used in the present invention can be produced by, for example, reacting a mono- or diglyceride with a polycarboxylic acid or a reactive derivative of the same.

Although the fatty acid residue constituting the monoglyceride of the present invention is not particularly restricted, it is preferable to use saturated or unsaturated fatty acid residues having from 8 to 22 carbon atoms, still preferably from 12 to 18 carbon atoms, therefor.

The fatty acid residues constituting the diglyceride are not particularly restricted too. It is preferable to use therefor a mixture of the above-mentioned fatty acid residue constituting the monoglyceride with one or more polycarboxylic acid residues as will be described hereinafter. Particularly preferable examples of the fatty acid residues of the mono- or diglyceride include lauric acid, stearic acid, oleic acid, linoleic acid and linolenic acid. In the case of the diglyceride, use may be made of a mixture of two of the above-mentioned fatty acid residues. The mono- or diglyceride may be either a monoglyceride, a diglyceride or a mixture thereof. Moreover, a triglyceride may be contained therein.

The polycarboxylic acid to be used in the present invention is not particularly restricted. Examples thereof include saturated dicarboxylic acid such as oxalic acid, malonic acid, succinic acid, glutaric acid, adipic acid, pimelic acid, suberic acid and azelaic acid; unsaturated dicarboxylic acids such as maleic acid, methylmaleic acid, fumaric acid and methylfumaric acid; hydroxypolycarboxylic acids such as malic acid, tartaric acid and citric acid; and esterified polycarboxylic acids prepared by esterifying all or some of hydroxyl groups of a hydroxycarboxylic acid with acetic acid or the above-mentioned carboxylic acids such as oxalic acid (for example, diacetyltartaric acid).

As the reactive derivatives of polycarboxylic acids, it is preferable to use acid anhydrides. Examples of such acid anhydrides include diacetyltartaric anhydride, maleic anhydride, phthalic anhydride and succinic anhydride. It is particularly preferable to use diacetyltartaric anhydride or succinic anhydride therefor.

The esterification of the mono- or diglyceride with the polycarboxylic acid or a reactive derivative thereof (hereinafter referred to as "polycarboxylic acids") is not particularly restricted. It may be carried out by mixing the mono- or diglyceride with the polycarboxylic acids and treated the mixture at a temperature of 85° to 200° C. for 0.1 to 3 hours. It is preferable to use from 0.1 to 10 parts by mol of the polycarboxylic acids per part of the mono- or diglyceride.

It is also possible to carry out the esterification in the presence of an amine such as pyridine and a basic catalyst. Thus the reaction can be completed at a lower temperature within a shorter period of time.

The ester obtained by the above-mentioned reaction can be used as such as a bitterness-relieving agent. The reaction product may contain the ester of the monoglyceride with the polycarboxylic acid or a salt thereof together with the ester of the diglyceride with the polycarboxylic acid or a salt thereof and the ratio of these components is not particularly restricted.

It may further contain the unreacted polycarboxylic acid and mono- or diglyceride and polymerization products thereof. However, it is preferable to purify the reaction product so as to regulate the content of the components other than the ester of the mono- or diglyceride with the polycarboxylic acid or a salt thereof to not more than 80% by weight, still preferably not more than 50% by weight and still preferably not more than 30% by weight, and particularly preferably not more than 5% by weight.

The reaction product may be purified by using a hydrophobic adsorption column (for example, silica gel column chromatography), a molecular weight fractionation column (for example, gel chromatography), etc.

Furthermore, the ester of the mono- or diglyceride with the polycarboxylic acid or a salt thereof may contain a carboxyl group having a free proton, so long as the carboxyl group does not participate in the reaction. Examples of the counter ion for the formation of the salt include alkali metals and alkaline earth metals such as sodium, potassium, calcium and magnesium, and aluminum. Sodium and potassium are particularly preferable therefor. A salt with an amino acid is also usable.

When the above-mentioned ester thus obtained is in the form of a powder, it can be used as such as the ester contained in the bitterness-relieving agent of the present invention. When the obtained ester is in the form of a liquid, it may be processed into a powder by mixing with, for example, protein, starch, saccharide or polymeric cellulose before using. When the above-mentioned ester has an unsaturated fatty acid residue, an antioxidant may be added thereto so as to prevent oxidation. As the antioxidant, use can be made of, for example, tocopherol acetate (for example, Sankatol™, manufactured by Taiyo Kagaku Co., Ltd.; Sankanon SD™, manufactured by Maruzen Kasei; Sanmelin™, manufactured by Saneigen AFI).

It is also possible to dissolve the above-mentioned ester in an edible oil (triglyceride) before using. For example, use can be made of vegetable fats and oils such as soybean oil, rapeseed oil, corn oil, palm oil, cottonseed oil, coconut oil, palm kernel oil, rice oil, sesame oil, safflower oil, high-oleic safflower oil, sunflower oil and high-oleic sunflower oil; animal fats and oils such as beef tallow, lard, fish oil, whale oil and milk fat; those obtained by fractionating these fats and oils; those obtained by hydrogenating the same; and those obtained by transesterifying the same. Either one of these fats and oils or a combination therof may be used.

When the above-mentioned ester is employed as a bitterness-relieving agent, a surfactant may be used together with it. Examples of the surfactant include sucrose fatty acid esters, polyglycerol fatty acid esters, sorbitan fatty acid esters, polyglycerol condensed ricinoleic acid ester, lecithin, polyoxyethylene-hardened castor oil, polyethylene glycol fatty acid esters, glycerol fatty acid esters and polyoxyethylene-based nonionic surfactants.

When added to medicinal compositions for oral use, foods, cosmetics or feeds tasting bitter, the bitterness-relieving agent of the present invention can relieve the bitterness.

The medicinal compositions for oral use, foods, cosmetics and feeds tasting bitter, to which the bitterness-relieving agent of the present invention is to be added, may be in arbitrary forms, for example, liquids (for example, aqueous solution, suspension, emulsion), pastes or solids (for example, powder). Also, the bitterness-relieving agent may be added in an arbitrary manner without restriction. When the medicinal composition for oral use, food, cosmetic or feed tasting bitter is in the form of a liquid (for example, aqueous solution, suspension, emulsion) or a paste, the bitterness-relieving agent of the present invention may be added thereto followed by thoroughly stirring and dispersing. The stirring and dispersion may be performed by using a homogenizer, an emulsifier, an ultrasonic treatment device, etc. The dispersion thus obtained may be dried by spray drying, freeze-drying, etc. to give a powdery or granular solid product. When the medicinal composition for oral use, food, cosmetic or feed tasting bitter is a solid matter (for example, powder), the bitterness-relieving agent of the present invention may be added thereto followed by mixing. Alternatively, the above-mentioned bitterness-relieving agent is dispersed in water, etc. and then mixed with the medicinal composition for oral use, food, cosmetic or feed tasting bitter in the form of a solid. Then the resulting mixture is homogenized and dehydrated. When the medicinal composition for oral use, food, cosmetic or feed tasting bitter is hardly soluble in water, it may be dissolved and/or dispersed with the use of an organic solvent (for example, hexane, ethyl acetate) or an alcohol (for example, ethanol) followed by the addition of the bitterness-relieving agent of the present invention.

The medicinal composition for oral use tasting bitter, to which the bitterness-relieving agent of the present invention is to be added, is not particularly restricted. Namely, any medicinal composition having bitter taste is usable therefor. Examples thereof include basic drugs such as promethazine, propranolol, berberine, chlorpromazine, chlorphenylamine, papaverine, thiamine and quinine; mineral acid salts of the basic drugs such as hydrochloride, nitrate, sulfate, acetate, citrate and carbonate; organic acid salts of the basic drugs such as maleate; Chinese orthodox drug preparations or crude drug preparations such as coptis rhizome, swertia, cinnamon bark, sophora root, *Phellodendron amurense RUPR.*, safflower, rhubarb, scutellaria root, phellodendron bark, gymnema, aloe, *Ginkgo biloba L.*, chlorella and jujube.

The medicinal composition for oral use containing the bitterness-relieving agent of the present invention may be in various dosage forms without restriction. Examples thereof include solid preparations such as capsules, granules, fine subtilaes, pills, dusts, tablets, freeze drying agents, troches, chewable tablets and dry syrups; and liquid preparations such as solutions, extracts, elixirs, spirits, syrups, aromatic waters, lemonades and fluidextracts.

These preparations may be produced by publicly known methods. For example, the bitterness-relieving agent of the present invention is mixed with one or more additives (for example, fillers, binders, disintegrating agents, lubricants, fluidizing agents, coatings, corrigents, masking agents, perfumes) and treated with a granulator (for example, planetary mixer, stirring granulator, high-speed mixing granulator, extrusion granulator, fluidized bed granulator, centrifugal rolling granulator, roller compactor) and/or a spray drying apparatus or a freeze drying apparatus.

The content of the bitterness-relieving agent of the present invention in the medicinal composition preferably ranges from 0.01 to 10% by weight, particularly preferably from 0.01 to 5% by weight and still preferably from 0.1 to 3% by weight. Per part by weight of the bitterness component in the medicinal composition, the content of the bitterness-relieving agent of the present invention preferably ranges from 0.01 to 1,000 parts by weight, particularly preferably from 0.1 to 100 parts by weight.

The food tasting bitter to which the bitterness-relieving agent of the present invention is to be added is not particularly restricted. Examples thereof include citrus fruits (for example, grapefruit, orange, lemon) and fruit juices containing the same; vegetables (for example, tomato, green pepper, celery, gourd, carrot, potato, asparagus) and vegetable juices containing the same; seasonings (for example, sauce, soy sauce, miso, stock seasonings, red pepper); processed soybean products (for example, soybean milk); emulsified foods (for example, cream, dressing, mayonnaise, margarine); fish meat and processed fish products (for example, ground fish meat, fish roe); nuts (for example, peanut); fermented foods (for example, natto); meat and processed meat products; drinks (for example, beer, whisky, coffee, cocoa, tea, green tea, fermented tea, semi-fermented tea, soft drinks, functional drinks); pickles; noodles; soups including powdery soup; dairy products (for example, cheese, cow's milk); bread and cakes; confectionery (for exmaple, snack, chewing gum, chocolate); candies; cigarettes; and health foods. It is also possible to add the bitterness-relieving agent of the present invention to a flavor to be used in foods to thereby relieve the bitterness of the flavor. In the case of food, the bitterness-relieving agent of the present invention is to be used to control the bitterness since the bitterness is sometimes an important flavor component for the food. It is furthermore possible to relieve the bitterness of amino acids tasting bitter (for example, leucine, isoleucine, phenylalanine), peptides and oligosaccharides by adding the bitterness-relieving agent of the present invention thereto.

Moreover, the bitterness-relieving agent of the present invention can be added in order to control the bitterness of a food which has a favorable bitterness. Examples of such a food include luxury drinks (for example, coffee, black tea, green tea); alcoholic drinks (for example, beer, whisky); some soft drinks (for example, vegetable juice); and spicy vegetables (for example, edible wild plants). The bitterness-relieving agent of the present invention is also usable in the step of boiling spicy vegetables or root vegetables to remove the harsh taste.

The content of the bitterness-relieving agent of the present invention in the food preferably ranges from 0.01 to 10% by weight, particularly preferably from 0.01 to 5% by weight and still preferably from 0.1 to 3% by weight. Regulated with the other standard, per part by weight of the bitterness component in the food, the content of the bitterness-relieving agent of the present invention preferably ranges from 0.1 to 1,000 parts by weight, particularly preferably from 0.1 to 50 parts by weight.

The cosmetic having bitter taste to which the bitterness-relieving agent of the present invention is to be added is not particularly restricted. Examples thereof include facial cosmetics (for example, lotion, milky lotion, cream, pack, lipstick, foundation, shaving cream, after shaving lotion, cleansing foam, cleansing gel); and oral cosmetics (for example, toothpaste, mouse wash, mouse rinse).

Examples of the bitterness component include surfactants (for example, sodium alkylsulfate, sodium monoalkylphosphate), flavors (for example, menthol, linalol, phenylethyl alcohol, ethyl propionate, geraniol, linalyl acetate, benzyl acetate), bactericides (for example, methylparaben, propylparaben, butylparaben), humectants (for example, lactic acid, sodium lactate), alcohol-denaturing agents (for example, 8-acetylated sucrose, brucine), and astringents (for example, aluminum lactate).

The content of the bitterness-relieving agent of the present invention in the cosmetic preferably ranges from 0.01 to 10% by weight, particularly preferably from 0.01 to 5% by weight, still preferably from 0.1 to 3% by weight. Per part by weight of the bitterness component in the cosmetic, the content of the bitterness-relieving agent of the present invention preferably ranges from 0.1 to 1,000 parts by weight, particularly preferably from 0.1 to 50 parts by weight.

The bitterness-relieving agent of the present invention, which can be obtained by a convenient method and exhibits an excellent effect of relieving bitterness, can be used in medicinal compositions for oral use, foods, cosmetics and feeds having bitterness components.

It is also possible to relive the bitterness or modify the taste by administering the medicinal compositions for oral use, foods, cosmetics and feeds containing the bitterness-relieving agent of the present invention to man or animals.

To further illustrate the present invention in greater detail, and not by way of limitation, the following Examples will be given.

Unless otherwise noted, all contents are expressed in % by weight.

REFERENTIAL EXAMPLE 1

Glycerol monostearate with a high purity (purity: 93% or above, EXCEL™ T-95, manufactured by Kao Corporation) and succinic anhydride were mixed together at a ratio of 1:1 (by mol) and esterified under stirring at 95° to 120° C. for 1 hour. Thus a component A containing an ester of the monoglyceride with succinic anhydride was obtained.

REFERENTIAL EXAMPLE 2

Glycerol dilaurate with a high purity (purity: 75%) and succinic anhydride were mixed together at a ratio of 1:1 (by mol) and esterified under stirring at 95° C. for 1 hour. Thus a component B containing an ester of the diglyceride with succinic anhydride was obtained.

REFERENTIAL EXAMPLE 3

Glycerol monostearate with a moderate purity (purity: 50% or above, EXCEL™ 150, manufactured by Kao Corporation) and succinic anhydride were mixed together at a ratio of 1:1 (by mol) and esterified under stirring at 95° C. for 1 hour. Thus a component C containing an ester of the diglyceride with succinic anhydride and another ester of the monoglyceride with succinic anhydride was obtained.

REFERENTIAL EXAMPLE 4

The procedure of Referential Example 2 was repeated but substituting the succinic anhydride by diacetyltartaric anhydride to thereby give a component D containing an ester.

REFERENTIAL EXAMPLE 5

The procedure of Referential Example 2 was repeated but substituting the succinic anhydride by maleic anhydride to thereby give a component E containing an ester.

REFERENTIAL EXAMPLE 6

The procedure of Referential Example 2 was repeated but substituting the succinic anhydride by citric acid to thereby give a component F containing an ester.

REFERENTIAL EXAMPLE 7

The component C obtained in Referential Example 3 was adjusted to pH 7 to 9 with sodium bicarbonate to thereby give a component G.

REFERENTIAL EXAMPLE 8

The component C obtained in Referential Example 3 was purified by silica gel chromatography to thereby give an ester component H having an elevated purity.

EXAMPLE 1

Each liquid preparation of the composition as given in Table 1 was produced by using propranolol hydrochloride having a strong bitterness. Next, the preparation was adjusted to pH 5.5 with the use of a citrate buffer and water was added thereto in such a manner as to give a total volume of 50 ml. For comparison, liquid preparations were produced in the same manner but substituting the bitterness-relieving agent of the present invention by monoglyceride, diglyceride and soybean lecithin. Further, a control preparation containing no bitterness-relieving agent was produced (the same will apply in the following Examples). Then the bitterness intensity of each liquid preparation was evaluated. Table 2 summarizes the results.

[Evaluation method]

To evaluate the bitterness intensity, a sensory test was effected with the use of 10 male and female panelists of twenties to forties in age. The bitterness was evaluated in 6 grades in accordance with the following criteria and expressed in the average.

Bitterness intensity 6: extremely bitter.
Bitterness intensity 5: very bitter.
Bitterness intensity 4: bitter, but not so strong.
Bitterness intensity 3: slightly bitter.
Bitterness intensity 2: noticeably bitter.
Bitterness intensity 1: not bitter.

TABLE 1

| | |
|---|---|
| propranolol hydrochloride | 10 mg |
| sucrose | 15 mg |
| butyl parahydroxybenzoate | 4 mg |
| Emanon CH60K (manufactured by Kao Co.) | 100 mg |
| d-α-tocopherol acetate | 100 mg |
| bitterness-relieving agent A–H | 0.5 or 1.5% |

TABLE 2

| | Bitterness intensity (average) Addition level | |
|---|---|---|
| Additive | 0.5% | 1.5% |
| bitterness-relieving agent A | 4.6 | 3.8 |
| bitterness-relieving agent B | 3.8 | 2.4 |
| bitterness-relieving agent C | 4.2 | 3.1 |
| bitterness-relieving agent D | 3.9 | 2.6 |
| bitterness-relieving agent E | 3.4 | 2.1 |
| bitterness-relieving agent F | 4.0 | 2.9 |
| bitterness-relieving agent G | 4.4 | 3.0 |
| bitterness-relieving agent H | 4.1 | 2.3 |
| monoglyceride | 5.7 | 5.4 |
| diglyceride | 5.4 | 5.0 |
| soybean lecithin | 5.0 | 4.6 |
| control | 5.9 | |

The results given in Table 2 clearly show that the bitterness can be relieved by using the bitterness-relieving agents of the present invention.

EXAMPLE 2

The procedure of Example 1 was repeated but substituting the propranolol hydrochloride by the following drugs to thereby give preparations. Each liquid preparation was easy to take, since the characteristic bitter taste had disappeared.

Drugs employed:

quinine, promethazine, papaverine, chlorpromazine, berberine, brucine, strychnine, vitamins, Chinese orthodox drugs or crude drugs.

EXAMPLE 3

A granular preparation containing quinine hydrochloride, the composition of which is given in Table 3, was prepared by the extrusion granulation method. Also, comparative preparations were prepared by substituting the bitterness-relieving agent of the present invention by monoglyceride and lecithin.

The control preparation (free from any additive) contained 60 parts of lactose. Table 4 summarizes the results.

TABLE 3

| | (part) |
|---|---|
| quinine hydrochloride (principal agent) | 1 |
| α-starch | 7 |
| corn starch | 32 |
| lactose | 55 |
| bitterness-relieving agents A to H | 5 |

TABLE 4

| Granular preparation | Bitterness intensity (average) |
| --- | --- |
| control | 6.0 |
| bitterness-relieving agent A | 4.7 |
| bitterness-relieving agent B | 3.6 |
| bitterness-relieving agent C | 3.9 |
| bitterness-relieving agent D | 3.7 |
| bitterness-relieving agent E | 3.4 |
| bitterness-relieving agent F | 4.0 |
| bitterness-relieving agent G | 4.1 |
| bitterness-relieving agent H | 3.8 |
| monoglyceride | 5.5 |
| lecithin | 5.2 |

By using the bitterness-relieving agent A to H of the present invention, the bitterness of the granular preparations tasting bitter could be further relieved.

EXAMPLE 4

The procedure of Example 3 was repeated but substituting the quinine hydrochloride by the following drugs to thereby give granular preparations. By using the bitterness-relieving agents of the present invention, the bitterness could be relieved.

Drugs employed:
promethazine, chlorpromazine, papaverine, propranolol, berberine, vitamins, Chinese orthodox drugs or crude drugs.

EXAMPLE 5

The procedure of Example 3 was repeated but substituting the quinine hydrochloride by promethazine, chlorpromazine, papaverine, propranolol or berberine and the processing each composition into not granules but tablets.

As a result, the bitterness could be relieved by using the bitterness-relieving agent of the present invention.

EXAMPLE 6

A granular preparation containing quinine hydrochloride, the composition of which is given in Table 5, was produced by the rolling granulation method. Also, a comparative preparation was produced by the same method but substituting the bitterness-relieving agent of the present invention by monoglyceride.

The control preparation (free from any additive) contained 59 parts of mannitol.

TABLE 5

|  | (part) |
| --- | --- |
| quinine hydrochloride (principal agent) | 1 |
| corn starch | 33 |
| mannitol | 58 |
| hydroxypropyl cellulose (15%) | 3.5 |
| bitterness-relieving agents A to H | 1 |

Compared with the comparative and control products, those containing the bitterness-relieving agents of the present invention showed each a relieved bitterness.

Furthermore, granular preparations were prepared by the same method but substituting the quinine hydrochloride by promethazine, chlorpromazine, papaverine, propranolol, berberine, vitamins, Chinese orthodox drugs or crude drugs. The results thus obtained were the same as those described above.

EXAMPLE 7

The bitterness-relieving agents A to H were added to a dry syrup, to be dissolved before using, containing quinine hydrochloride as the principal agent.

Also, dry syrups were produced by the same method as the above-mentioned one but substituting the quinine hydrochloride by promethazine, chlorpromazine, papaverine, propranolol, berberine, vitamins, Chinese orthodox drugs or crude drugs.

Compared with the control product free from any bitterness-relieving agent, each preparation containing the bitterness-relieving agent of the present invention showed a relieved bitterness.

EXAMPLE 8

The bitterness-relieving agent B was added to drip coffee to thereby give a coffee with a regulated bitterness. Also, a comparative product was prepared in the same manner but substituting the bitterness-relieving agent B by lecithin. Table 6 summarizes the results.

TABLE 6

| Product | Bitterness intensity |
| --- | --- |
| control | 3.8 |
| containing 0.01% of bitterness-relieving agent B | 3.3 |
| containing 0.1% of bitterness-relieving agent B | 2.6 |
| containing 1.0% of bitterness-relieving agent B | 1.7 |
| containing 0.1% of lecithin | 3.4 |

The results given in Table 6 indicate that the bitterness of coffee can be further relieved by using the bitterness-relieving agent B in an appropriate amount. Moreover, the coffee thus obtained showed a mild flavor.

EXAMPLE 9

The procedure of Example 8 was repeated but substituting the bitterness-relieving agent B by the bitterness-relieving agent G. Thus, the bitterness could be relieved by using the bitterness-relieving agent G.

EXAMPLE 10

The bitterness-relieving agent C was added to vegetable juice, orange juice and grapefruit juice. Table 7 shows the results.

TABLE 7

| Product | Bitterness intensity |
| --- | --- |
| vegetable juice | 3.8 |
| vegetable juice containing 0.1% of bitterness-relieving agent C | 3.0 |
| vegetable juice containing 0.5% of bitterness-relieving agent C | 1.7 |
| orange juice | 3.5 |
| orange juice containing 0.1% of bitterness-relieving agent C | 3.0 |
| orange juice containing 0.5% of bitterness-relieving agent C | 1.1 |
| grapefruit juice | 4.0 |
| grapefruit juice containing 0.1% of bitterness-relieving agent C | 3.2 |

TABLE 7-continued

| Product | Bitterness intensity |
| --- | --- |
| grapefruit juice containing 0.5% of bitterness-relieving agent C | 1.4 |

As Table 7 shows, the bitterness of each juice was thus relieved.

EXAMPLE 11

0.3% of the bitterness-relieving agent B was dissolved in rapeseed oil and whipped cream was prepared by using this rapeseed oil. The whipped cream thus obtained showed an improved flavor.

EXAMPLE 12

0.1% of the bitterness-relieving agent G was added to water and dispersed therein. In the water thus obtained, burdock, lotus root, bamboo shoot and bracken were boiled to remove the harsh taste.

As a result, each vegetable thus treated showed an improved flavor.

EXAMPLE 13

The bitterness-relieving agent H was added to a cookie containing corn peptide which was a hydrolyzate of corn protein. Table 8 summarizes the results.

TABLE 8

| Product | Bitterness intensity |
| --- | --- |
| cookie | 4.3 |
| cookie containing 0.5% of bitterness-relieving agent H | 3.1 |
| cookie containing 2.0% of bitterness-relieving agent H | 1.4 |

As Table 8 shows, cookies having a relieved bitterness could be thus obtained.

EXAMPLE 14

The bitterness-relieving agents E, F and G were added to a candy containing caffeine and menthol. Also, comparative products were produced by substituting the bitterness-relieving agents by monoglyceride and citric acid. Table 9 summarizes the results.

TABLE 9

| Product | Bitterness intensity |
| --- | --- |
| candy | 5.1 |
| candy containing 1.0% of bitterness-relieving agent E | 3.1 |
| candy containing 1.0% of bitterness-relieving agent F | 3.4 |
| candy containing 1.0% of bitterness-relieving agent G | 3.3 |
| candy containing 1.0% of monoglyceride | 4.8 |
| candy containing 1.0% of citric acid | 4.4 |

As Table 9 shows, candies having a relieved bitterness could be thus obtained.

EXAMPLE 15

A tooth paste of the composition as given in Table 10 was prepared by a conventional method.

TABLE 10

| | (%) |
| --- | --- |
| calcium secondary phosphate.2H$_2$O | 45.0 |
| silicic anhydride | 2.0 |
| sorbitol | 15.0 |
| carboxymethyl cellulose | 1.5 |
| sodium monolaurate | 2.0 |
| flavor | q.s. |
| bitterness-relieving agent A | 2.0 |
| water | the balance |

In this toothpaste, the bitterness originating in sodium monolaurate had been relieved.

EXAMPLE 16

A mouth wash of the composition as given in Table 11 was prepared by a conventional method.

TABLE 11

| | (%) |
| --- | --- |
| ethanol | 15.0 |
| sorbitol | 10.0 |
| sodium saccharate | 0.15 |
| L-menthol | 0.10 |
| sodium lauryl sulfate | 0.10 |
| bitterness-relieving agent B | 1.0 |
| water | the balance |

In this mouth wash, the bitterness originating in L-menthol and sodium lauryl sulfate had been relieved.

EXAMPLE 17

A cosmetic lotion of the composition as given in Table 12 was prepared by a conventional method.

TABLE 12

| | (%) |
| --- | --- |
| glycerol | 5.0 |
| 1,3-butanediol | 5.0 |
| denatured ethanol (containing 0.1% of 8-acetylated sucrose) | 10.0 |
| polyoxyethylene (20) octyl dodecyl ether | 1.0 |
| perfume | q.s. |
| bitterness-relieving agent C | 0.5 |
| methylparaben | 0.1 |
| water | the balance |

In this cosmetic lotion, the bitterness originating in 8-acetylated sucrose had been relieved. After applying, therefore, the cosmetic lotion remaining around the mouth gave no sense of incongruity.

EXAMPLE 18

A cosmetic milky lotion of the composition as given in Table 13 was prepared by a conventional method.

TABLE 13

| | (%) |
| --- | --- |
| cyclic silicone (pentamer) | 20.0 |
| squalane | 5.0 |
| polyoxyethylene-denatured silicone | 5.0 |

TABLE 13-continued

|  | (%) |
| --- | --- |
| sodium lactate | 4.0 |
| methylparaben | 0.1 |
| perfume | q.s. |
| bitterness-relieving agent G | 2.0 |
| water | the balance |

In this cosmetic milky lotion, the bitterness originating in sodium lactate had been relieved. After applying, therefore, the cosmetic lotion remaining around the mouth gave no conspicuous bitterness.

EXAMPLE 19

A facial cleanser of the composition as given in Table 14 was prepared.

TABLE 14

|  | (%) |
| --- | --- |
| triethanolamine monolaurate | 20.0 |
| lauryl betaine | 5.0 |
| glycerol | 5.0 |
| polyoxyethylene (100) oleyl ether | 2.0 |
| bitterness-relieving agent E | 5.0 |
| water | the balance |

This facial cleanser gave no conspicuous bitterness, even though it was put into the mouth by mistake during cleansing.

EXAMPLE 20

A mouth freshener of the composition as given in Table 15 was prepared.

TABLE 15

|  | (%) |
| --- | --- |
| ethanol | 35.0 |
| glycerol | 10.0 |
| polyoxyethylene-hardened castor oil | 1.0 |
| L-menthol | 0.5 |
| chlorhexidine gluconate | 0.02 |
| bitterness-relieving agent H | 1.0 |
| water | the balance |

Although this mouth freshener contained a large amount of L-menthol, it showed an intense refreshing feel with little bitterness.

While the invention has been described in detail and with reference to specific examples thereof, it will be apparent to one skilled in the art that various changes and modifications can be made therein without departing from the spirit and scope thoereof.

What is claimed is:

1. A method for relieving the bitterness of a food which comprises administering to a man said food comprising an ester of a monoglyceride or diglyceride or mixtures of said esters, with a polycarboxylic acid or a salt thereof.

2. A method for relieving the bitterness of a medicinal composition which comprises administering to a man or an animal said medicinal composition comprising an ester of a monoglyceride or diglyceride or mixtures of said esters, with a polycarboxylic acid or a salt thereof.

3. A method for relieving the bitterness of a cosmetic composition which comprises administering to a man or an animal, said cosmetic composition comprising an ester of a monoglyceride or diglyceride or mixtures of said esters, with a polycarboxylic acid or a salt thereof.

4. A method for relieving the bitterness of a animal feed which comprises administering to an animal, said animal feed comprising an ester of a monoglyceride or diglyceride or mixtures of said esters, with a polycarboxylic acid or a salt thereof.

5. A method for modifying the taste of a food which comprises adding to said food an ester of a monoglyceride or diglyceride or mixtures of said esters, with a polycarboxylic acid or a salt thereof.

6. A method for modifying the taste of a medicinal composition which comprises adding to said medicinal composition an ester of a monoglyceride or diglyceride or mixtures of said esters, with a polycarboxylic acid or a salt thereof.

7. A method for modifying the taste of a cosmetic which comprises adding to said cosmetic an ester of a monoglyceride or diglyceride or mixtures of said esters, with a polycarboxylic acid or a salt thereof.

8. A method for modifying the taste of an animal feed which comprises adding to said animal feed an ester of a monoglyceride or diglyceride or mixtures of said esters, with a polycarboxylic acid or a salt thereof.

9. The method as claimed in claim 1, wherein said polycarboxylic acid is selected from the group consisting of diacetyltartaric acid, maleic acid, phthalic acid, citric acid and succinic acid, or mixtures thereof.

10. The method as claimed in claim 2, wherein said polycarboxylic acid is selected from the group consisting of diacetyltartaric acid, maleic acid, phthalic acid, citric acid and succinic acid, or mixtures thereof.

11. The method as claimed in claim 3, wherein said polycarboxylic acid is selected from the group consisting of diacetyltartaric acid, maleic acid, phthalic acid, citric acid and succinic acid, or mixtures thereof.

12. The method as claimed in claim 4, wherein said polycarboxylic acid is selected from the group consisting of diacetyltartaric acid, maleic acid, phthalic acid, citric acid and succinic acid, or mixtures thereof.

13. The method as claimed in claim 5, wherein said polycarboxylic acid is selected from the group consisting of diacetyltartaric acid, maleic acid, phthalic acid, citric acid and succinic acid, or mixtures thereof.

14. The method as claimed in claim 6, wherein said polycarboxylic acid is selected from the group consisting of diacetyltartaric acid, maleic acid, phthalic acid, citric acid and succinic acid, or mixtures thereof.

15. The method as claimed in claim 7, wherein said polycarboxylic acid is selected from the group consisting of diacetyltartaric acid, maleic acid, phthalic acid, citric acid and succinic acid, or mixtures thereof.

16. The method as claimed in claim 8, wherein said polycarboxylic acid is selected from the group consisting of diacetyltartaric acid, maleic acid, phthalic acid, citric acid and succinic acid, or mixtures thereof.

17. The method as claimed in claim 1, wherein fatty acid residues of said diglyceride are saturated or unsaturated fatty acid residues having 8 to 22 carbon atoms or mixtures thereof.

18. The method as claimed in claim 2, wherein fatty acid residues of said diglyceride are saturated or unsaturated fatty acid residues having 8 to 22 carbon atoms or mixtures thereof.

19. The method as claimed in claim 3, wherein fatty acid residues of said diglyceride are saturated or unsaturated fatty acid residues having 8 to 22 carbon atoms or mixtures thereof.

20. The method as claimed in claim 4, wherein fatty acid residues of said diglyceride are saturated or unsaturated fatty acid residues having 8 to 22 carbon atoms or mixtures thereof.

21. The method as claimed in claim 5, wherein fatty acid residues of said diglyceride are saturated or unsaturated fatty acid residues having 8 to 22 carbon atoms or mixtures thereof.

22. The method as claimed in claim 6, wherein fatty acid residues of said diglyceride are saturated or unsaturated fatty acid residues having 8 to 22 carbon atoms or mixtures thereof.

23. The method as claimed in claim 7, wherein fatty acid residues of said diglyceride are saturated or unsaturated fatty acid residues having 8 to 22 carbon atoms or mixtures thereof.

24. The method as claimed in claim 8, wherein fatty acid residues of said diglyceride are saturated or unsaturated fatty acid residues having 8 to 22 carbon atoms or mixtures thereof.

25. The method as claimed in claim 1, wherein a fatty acid residue of said monoglyceride is a saturated or unsaturated fatty acid residue having 8 to 22 carbon atoms.

26. The method as claimed in claim 2, wherein a fatty acid residue of said monoglyceride is a saturated or unsaturated fatty acid residue having 8 to 22 carbon atoms.

27. The method as claimed in claim 3, wherein a fatty acid residue of said monoglyceride is a saturated or unsaturated fatty acid residue having 8 to 22 carbon atoms.

28. The method as claimed in claim 4, wherein a fatty acid residue of said monoglyceride is a saturated or unsaturated fatty acid residue having 8 to 22 carbon atoms.

29. The method as claimed in claim 5, wherein a fatty acid residue of said monoglyceride is a saturated or unsaturated fatty acid residue having 8 to 22 carbon atoms.

30. The method as claimed in claim 6, wherein a fatty acid residue of said monoglyceride is a saturated or unsaturated fatty acid residue having 8 to 22 carbon atoms.

31. The method as claimed in claim 7, wherein a fatty acid residue of said monoglyceride is a saturated or unsaturated fatty acid residue having 8 to 22 carbon atoms.

32. The method as claimed in claim 8, wherein a fatty acid residue of said monoglyceride is a saturated or unsaturated fatty acid residue having 8 to 22 carbon atoms.

33. The method according to claim 1, wherein said ester of a monoglyceride or diglyceride or mixture of said esters, with a polycarboxylic acid or salt thereof is present in an amount of from 0.01 to 10% by weight based on the weight of said food.

34. The method according to claim 5, wherein said ester of a monoglyceride or diglyceride or mixture of said esters, with a polycarboxylic acid or salt thereof is present in an amount of from 0.01 to 10% by weight based on the weight of said food.

35. The method according to claim 2, wherein said ester of a monoglyceride or diglyceride or mixture of said esters, with a polycarboxylic acid or salt thereof is present in an amount of from 0.01 to 10% by weight based on the weight of said medicinal composition.

36. The method according to claim 6, wherein said ester of a monoglyceride or diglyceride or mixture of said esters, with a polycarboxylic acid or salt thereof is present in an amount of from 0.01 to 10% by weight based on the weight of said medicinal composition.

37. The method according to claim 3, wherein said ester of a monoglyceride or diglyceride or mixture of said esters, with a polycarboxylic acid or salt thereof is present in an amount of from 0.01 to 10% by weight based on the weight of said cosmetic composition.

38. The method according to claim 7, wherein said ester of a monoglyceride or diglyceride or mixture of said esters, with a polycarboxylic acid or salt thereof is present in an amount of from 0.01 to 10% by weight based on the weight of said cosmetic composition.

* * * * *